US009366885B2

(12) United States Patent
Rubio Guivernau et al.

(10) Patent No.: US 9,366,885 B2
(45) Date of Patent: Jun. 14, 2016

(54) INTEGRATED DELAY LINE FOR OPTICAL COHERENCE TOMOGRAPHY

(75) Inventors: José Luis Rubio Guivernau, Madrid (ES); Eduardo Margallo Balbás, Madrid (ES)

(73) Assignee: Medlumics S.L., Madrid (ES)

( * ) Notice: Subject to any disclaimer, the term of this patent is extended or adjusted under 35 U.S.C. 154(b) by 42 days.

(21) Appl. No.: 14/129,367

(22) PCT Filed: Jun. 28, 2012

(86) PCT No.: PCT/EP2012/062624
§ 371 (c)(1),
(2), (4) Date: Dec. 26, 2013

(87) PCT Pub. No.: WO2013/001032
PCT Pub. Date: Jan. 3, 2013

(65) Prior Publication Data
US 2014/0118748 A1 May 1, 2014

(30) Foreign Application Priority Data

Jun. 28, 2011 (ES) .................................. 201131088

(51) Int. Cl.
*G01B 11/02* (2006.01)
*G02F 1/01* (2006.01)
(Continued)

(52) U.S. Cl.
CPC ............ *G02F 1/0115* (2013.01); *A61B 5/0066* (2013.01); *G01B 9/02058* (2013.01);
(Continued)

(58) Field of Classification Search
CPC .......... G01B 9/02091; G01B 9/02011; G01B 2290/70

USPC .......................................... 356/479, 491, 495
See application file for complete search history.

(56) References Cited

U.S. PATENT DOCUMENTS 5,930,414 A 7/1999 Fishman et al.
6,385,358 B1 5/2002 Everett et al.
(Continued)

FOREIGN PATENT DOCUMENTS

CN 1211744 A 3/1999
CN 1367593 A 9/2002
(Continued)

OTHER PUBLICATIONS

Cardenas, J., et al., "Wide-bandwidth continuously tunable optical delay line using silicon microring resonators," *Optics Express* 18(25):26525-26534, Optical Society of America, United States (2010).
(Continued)

*Primary Examiner* — Jonathan Hansen
(74) *Attorney, Agent, or Firm* — Sterne, Kessler, Goldstein & Fox P.L.L.C.

(57) ABSTRACT

A system includes a waveguide that guides a beam of radiation, a variable delay unit, and a polarization-dependent modulating unit. The variable delay unit modulates the refractive index in a region, and the waveguide makes a plurality of passes through the region. The polarization-dependent element compensates for birefringence associated with the beam of radiation and includes a polarization splitter and a plurality of modulating elements. The polarization splitter has a first arm and a second arm that each include modulation segments. The beam of radiation is split between the first arm and the second arm and recombined after traversing the modulation segments. The recombination of the beam generates a first polarized beam of radiation and a second polarized beam of radiation. The plurality of modulating elements apply a first and second modulation to the first polarized beam of radiation and the second polarized beam of radiation respectively.

35 Claims, 18 Drawing Sheets

(51) Int. Cl.
*A61B 5/00* (2006.01)
*G01B 9/02* (2006.01)
*G02B 6/35* (2006.01)
*G02B 6/293* (2006.01)

(52) U.S. Cl.
CPC ........ *G01B9/02091* (2013.01); *G02B 6/29352* (2013.01); *G02B 6/3586* (2013.01); *G01B 2290/40* (2013.01); *G01B 2290/70* (2013.01)

(56) References Cited

U.S. PATENT DOCUMENTS

| | | |
|---|---|---|
| 2003/0026518 A1 | 2/2003 | Pezeshki et al. |
| 2004/0101227 A1 | 5/2004 | Takabayashi et al. |
| 2007/0086017 A1 | 4/2007 | Buckland et al. |
| 2007/0285669 A1 | 12/2007 | Ajgaonkar et al. |
| 2008/0159681 A1 | 7/2008 | Gill et al. |
| 2009/0022443 A1 | 1/2009 | Chen et al. |
| 2010/0119189 A1 | 5/2010 | Nasu et al. |

FOREIGN PATENT DOCUMENTS

| | | |
|---|---|---|
| EP | 0 831 312 A1 | 3/1998 |
| WO | WO 2010/140363 A1 | 12/2010 |

OTHER PUBLICATIONS

Kobayashi, I., and Koruda, K., "Step-Type Optical Delay Line Using Silica-Based Planar Light-Wave Circuit (PLC) Technology," *IEEE Transactions on Instrumentation and Measurement* 49(4):762-765, IEEE, United States (2000).

Margallo-Balbás, E., et al., "Thermo-optical delay line for optical coherence tomography," *Proc. SPIE* 6717:671704, SPIE, the international Society for Optical Engineering, United States (2007).

Margallo-Balbás, E., et al., "Miniature 10 kHz theti o-optic delay line in silicon," *Opt. Lett.* 35(23):4027-4029, Optical Society of America, United States (2010).

Melloni, A., et al., "Determination of Bend Mode Characteristics in Dielectric Waveguides," *Journal of Lightwave Technology* 19(4): 571-577, IEEE, United States (2001).

International Search Report for International Patent Application No. PCT/EP2012/062624, European Patent Office, Rijswijk, Netherlands, mailed on Sep. 18, 2012.

Written Opinion for International Patent Application No. PCT/EP2012/062624, European Patent Office, Rijswijk, Netherlands, mailed on Sep. 18, 2012.

English Translation of Chinese Office Action with Search Report, mailed May 4, 2015, directed to Appl. No. 201280040162.7, filed Jun. 28, 2012; 13 pages.

English-Language Abstract of Chinese Patent Publication CN 1367593, filed Apr. 9, 2002; 1 page.

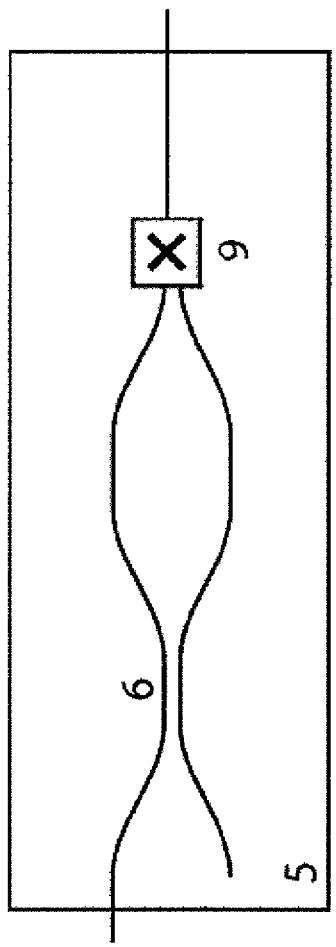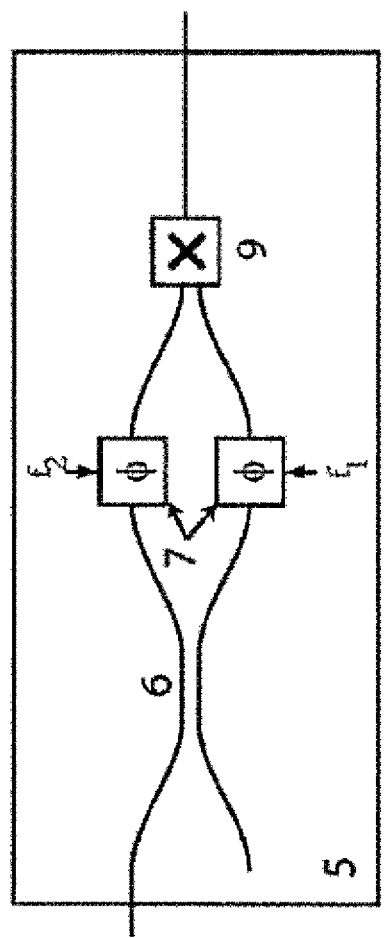
FIG. 8A
FIG. 8B

1800

INTEGRATED DELAY LINE FOR OPTICAL COHERENCE TOMOGRAPHY

BACKGROUND

1. Field

Embodiments of the invention relate to the use of variable delay lines in high-resolution optical coherence tomography.

2. Background

Optical Coherence Tomography (OCT) is a medical imaging technique providing depth resolved information with high axial resolution by means of a broadband light source and an interferometric detection system. It has found plenty of applications, ranging from ophthalmology and cardiology to gynecology and in-vitro high-resolution studies of biological tissues.

One of the elements in a Time Domain OCT (TD-OCT) system is the variable delay line, which may be used to perform the depth scan inside the sample. Several patents have described implementations of delay lines that are able to provide the necessary delay variation range at high scan speeds for their use in OCT. For example, patent application EP 0831312 describes a device based on an optical fiber and a piezoelectric element for its use as a variable delay line in OCT.

However, variable delay line implementations relying on mechanical elements have intrinsic limitations to their maximum operating speed that can be achieved, due to the use of moving parts and their inertia. Recently an implementation of a variable delay line based on integrated optics and taking advantage of silicon's thermo-optical effect has been described ("Thermo-optical delay line for optical coherence tomography" E. Margallo-Balbás, G. Pandraud, and P. J. French, Proc. SPIE 6717, 671704 (2007), "Miniature 10 kHz thermo-optic delay line in silicon" E. Margallo-Balbás, M. Geljon, G. Pandraud, and P. J. French, Opt. Lett. 35 (23). pp. 4027-4029 (2010). These references provide an overview of some advantages of using a thermo-optical delay line.

The thermo-optic effect is based on the variation in phase and group refractive indices of a material with temperature. The relationship between temperature change and refractive index variation is known as the thermo-optic coefficient. As an example, silicon exhibits a value of $2.4 \times 10^{-4} K^{-1}$ at room temperature for a wavelength of 1.3 µm, meaning that obtaining a change in optical path of 1 mm requires a temperature increase of 417K for a 1 cm waveguide segment. However, for a given fabrication technology, there is a compromise between the length of the waveguide subject to thermal action, the applied power, the maximum delay (determining the maximum scan depth) and the maximum frequency for thermal cycling (determining scan rate). This trade-off implies that thermal design choices are set once the production process is selected.

One way to relieve the aforementioned trade-off is to trace a waveguide segment several times over an area with a controllable refractive index as described in U.S. patent application publication No. 2009/0022443. Although emphasis is made of good waveguide curvature design to reduce power loss, there is no mention of how to compensate for other optical effects such as birefringence. Birefringence describes an existence of different propagation constants for each polarization mode in a waveguide. (A. Melloni et al., "Determination of Bend Mode Characteristics in Dielectric Waveguides", J. Lightwave Technol., vol. 19(4), pp. 571-577, 2001).

In many cases, solutions to birefringence are based on the optimization of the waveguide technology itself, such as designing the correct cross-sectional geometry or through the introduction of controlled stress levels to the waveguides. Materials such as thermal silicon oxide have been reported for introducing stress to adjust group and phase velocity of light within the waveguide.

Although these solutions are appropriate in some cases, they complicate the fabrication process and their value depends on tolerances in the deposition and microfabrication steps of the concerned layers. Additionally, they cannot compensate birefringence introduced by waveguide segments having a relatively strong curvature.

Other articles in the literature ("Step-type optical delay line using silica-based planar light-wave circuit (PLC) technology", I. Kobayashi and K. Koruda, IEEE Instrumentation and Measurement, 1998 and "Wide-bandwidth continuously tunable optical delay line using silicon microring resonators", J. Cardenas et al., Opt. Express 18, 26525-26534, 2010) report using the thermo-optic effect to produce integrated delay lines. In all cases, however, the application field is different and design parameters diverge significantly from what is required for OCT. Free spectral ranges (FSR) in applications such as telecom are several orders of magnitude smaller than the ones required for OCT. In the first article (Kobayashi et al.) a trade-off between FSR and maximum delay is reported, such that the device would only attain a FSR of approximately 150 GHz in an OCT application. In the second article (J. Cardenas et al.), the corresponding FSR is only 10 GHz. Both ranges are many orders of magnitude away from the ranges used in OCT, which typically utilize bandwidths in the tens of THz's.

BRIEF SUMMARY

A system that introduces a variable group delay to a beam of radiation while compensating for the effects of birefringence on the beam of radiation is presented. The use of the system within the scope of optical coherence tomography and the advantages gained by using such a system are also described.

In an embodiment, a system is presented that includes a waveguide for guiding a beam of radiation, a variable delay unit, and a polarization-dependent modulating unit. The variable delay unit modulates the refractive index in a region, and the waveguide makes a plurality of passes through the region. The polarization-dependent element compensates for birefringence associated with the beam of radiation and includes a polarization splitter and a plurality of modulating elements. The polarization splitter has a first arm and a second arm that each include modulation segments. The beam of radiation is split between the first arm and the second arm and recombined after traversing the modulation segments. The recombination of the beam generates a first polarized beam of radiation and a second polarized beam of radiation. The plurality of modulating elements apply a first and second modulation to the first polarized beam of radiation and the second polarized beam of radiation respectively.

In another embodiment, an optical coherence tomography system is presented. The system includes an optical source, an optical element, a variable delay unit, and an optical modulating unit. The optical source provides a beam of radiation. The optical element splits the beam of radiation between at least a first waveguide and a second waveguide. A first portion of the beam of radiation propagates through the first waveguide and a second portion of the beam of radiation propagates through the second waveguide. Both the variable delay unit and the optical modulating unit are associated with at least one of the first waveguide and the second waveguide.

The variable delay unit introduces a group delay to the associated portion of the beam of radiation and includes an index modulating element that modulates the refractive index in a region. The waveguide associated with the variable delay unit makes a plurality of passes through the region. The optical modulating unit includes a polarization splitter and a plurality of modulating elements. The polarization splitter splits the associated portion of the beam of radiation into at least a first polarized beam of radiation and a second polarized beam of radiation. The plurality of modulating elements apply a first and second modulation to the first polarized beam of radiation and the second polarized beam of radiation respectively.

An example method is described. In an embodiment, the method includes receiving a beam of radiation at a variable delay unit. The method further includes modulating the refractive index of a region within the variable delay unit. The beam of radiation is passed one or more times through the region. Birefringence is introduced to the beam of radiation via the passing. The method further includes receiving the beam of radiation at a modulating unit. The beam of radiation is split between a first arm and a second arm using a polarization splitter within the modulating unit. The method then includes generating a first polarized mode of the beam of radiation and a second polarized mode of the beam of radiation. The method further includes applying, using a plurality of modulating elements, a first modulation and a second modulation to the first polarized mode and the second polarized mode of the beam of radiation respectively. The applying further compensates for the birefringence associated with the beam of radiation.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

Figure 3A:
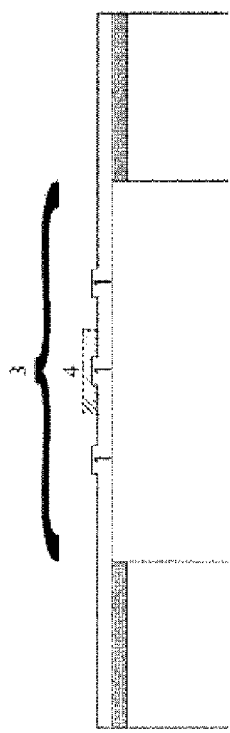
Figure 3B:
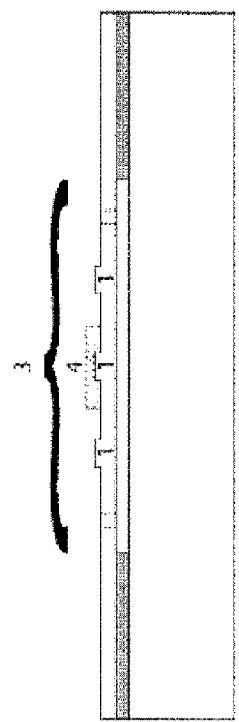
Figure 3C:
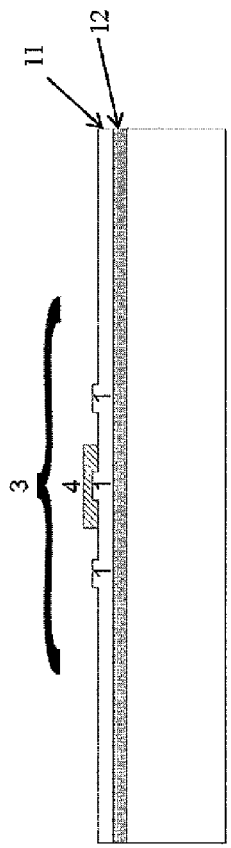

FIGS. 3A-C illustrate side views of a variable delay unit according to embodiments.

Figure 4:
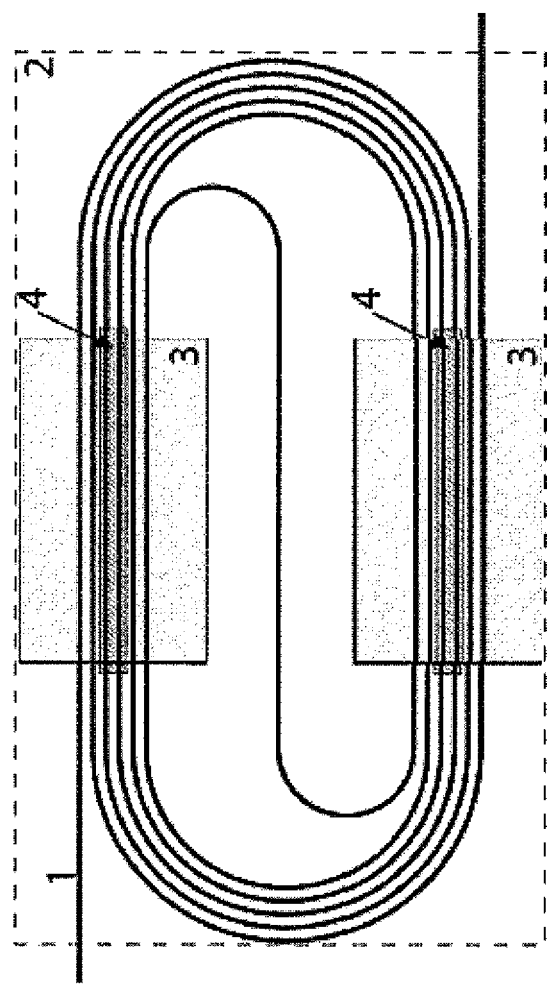

FIG. 4 illustrates a top view of a variable delay unit according to another embodiment.

Figure 5:
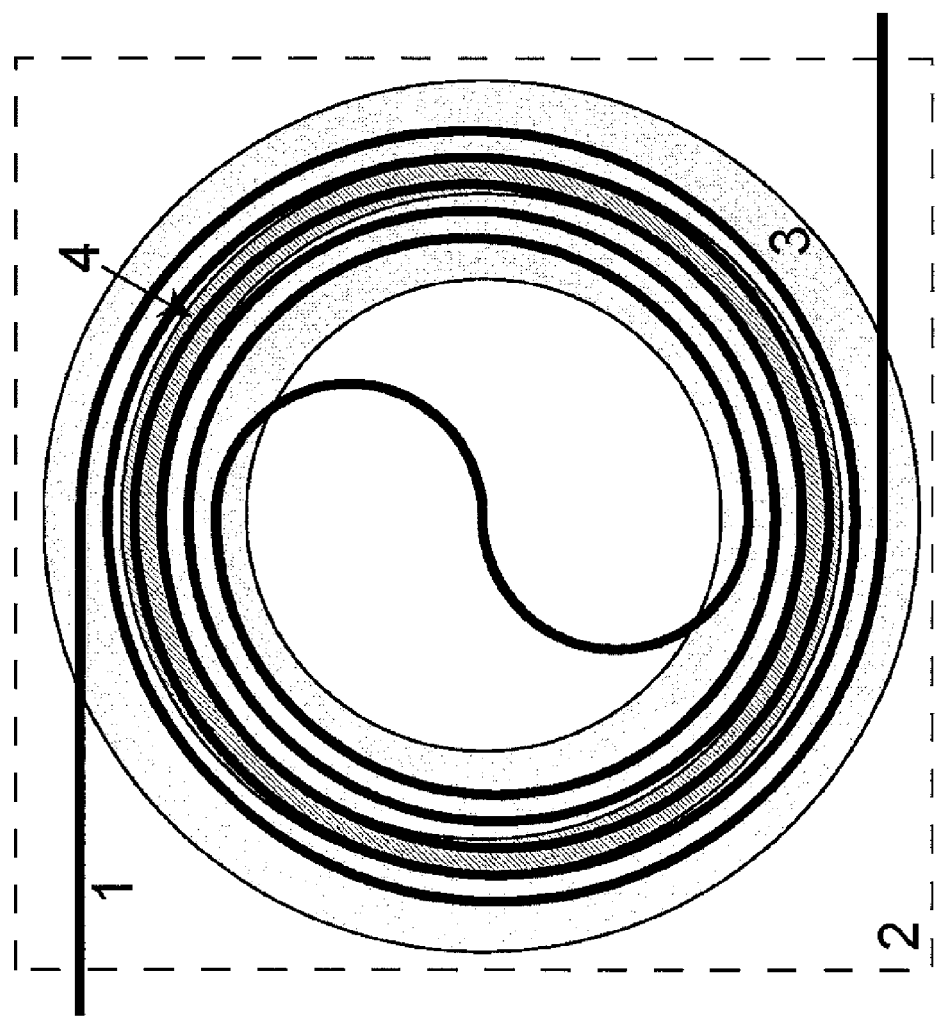

FIG. 5 illustrates a top view of a variable delay unit according to another embodiment.

Figure 6:
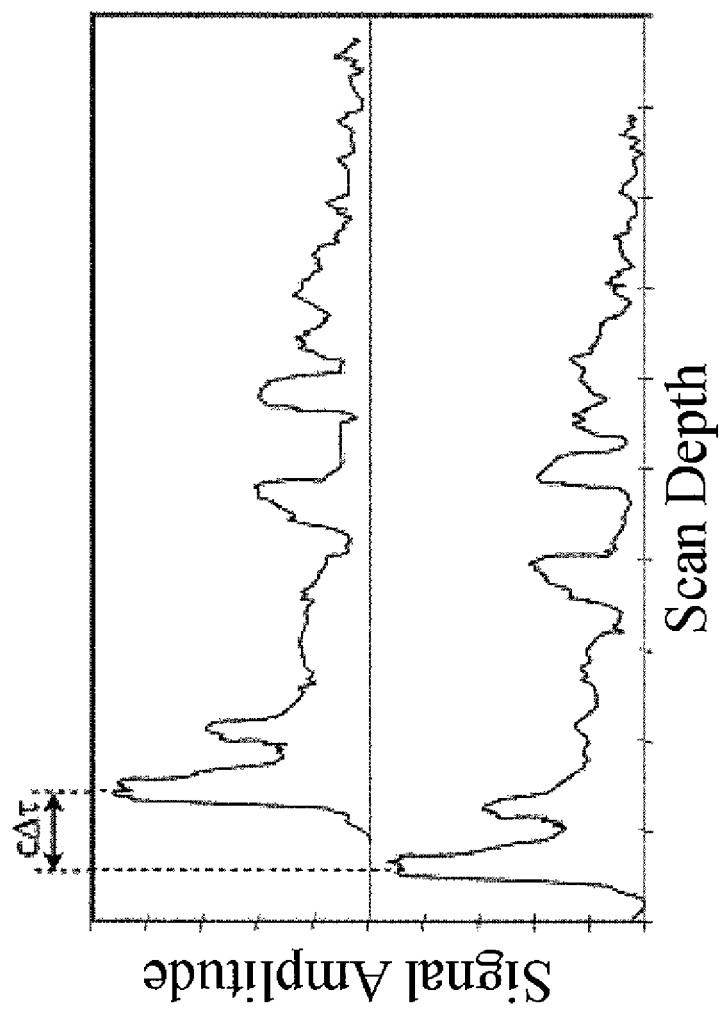

FIG. 6 illustrates an effect that birefringence has on an example signal received at a detector.

Figure 7:
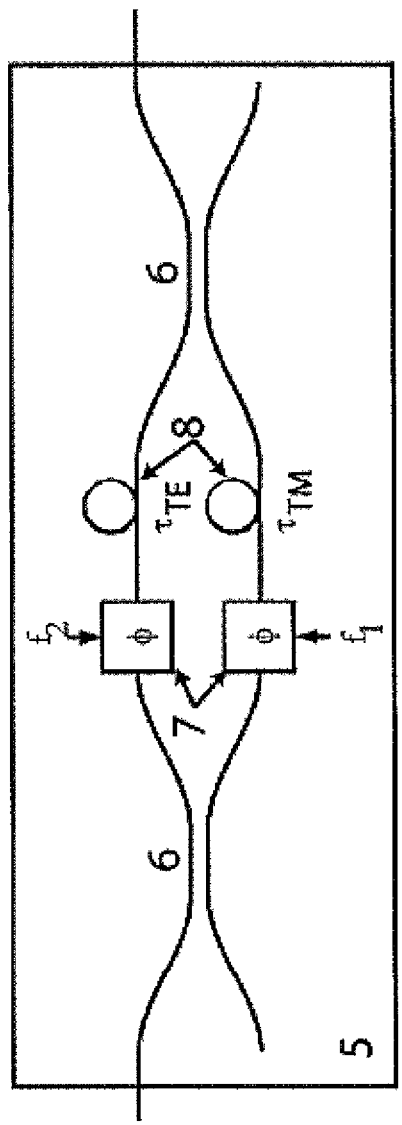

FIG. 7 illustrates an example of an optical modulating unit, according to an embodiment.

FIGS. 8A-B illustrate examples of optical modulating units having an optical switch, according to embodiments.

Figure 9:
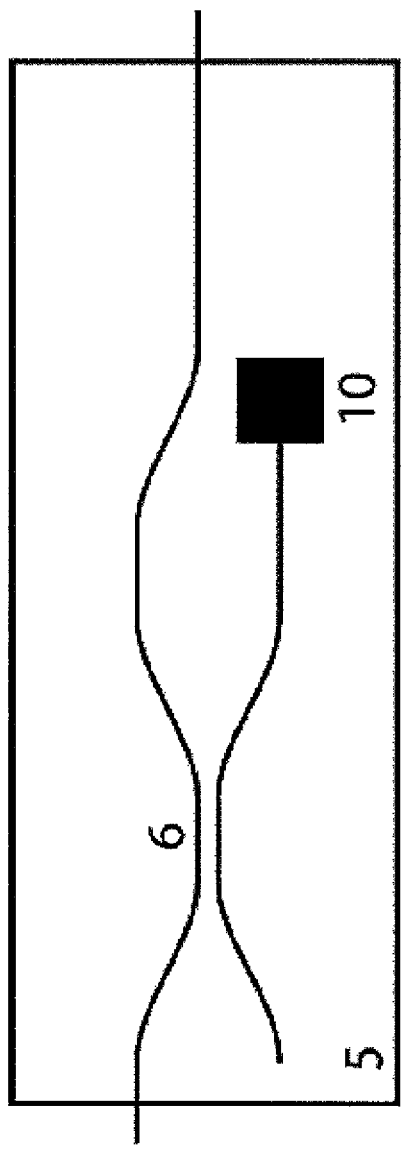

FIG. 9 illustrates an example of an optical modulating unit having an optical absorbing element, according to an embodiment.

Figure 10:
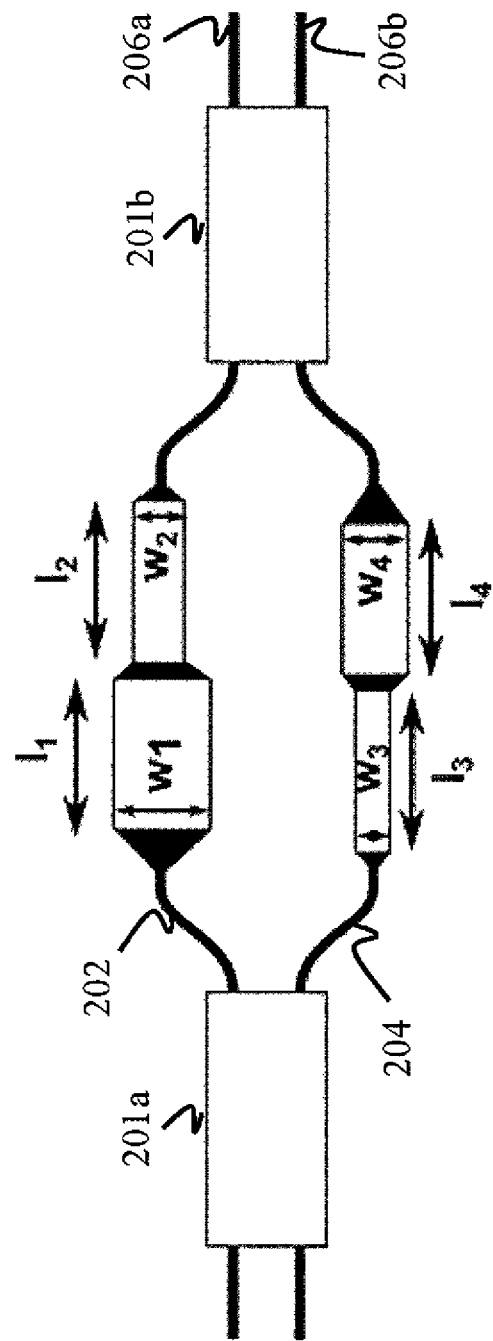

FIG. 10 illustrates an example design of a polarization splitter, according to an embodiment.

Figure 11:
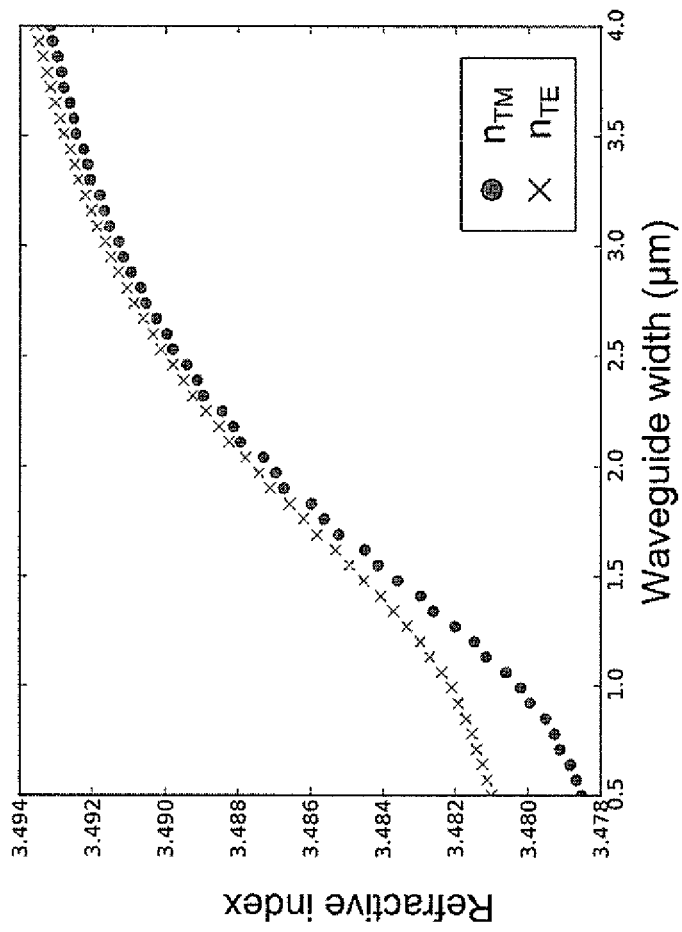

FIG. 11 illustrates a simulated effect that waveguide width has on refractive index for both polarization modes.

Figure 12:
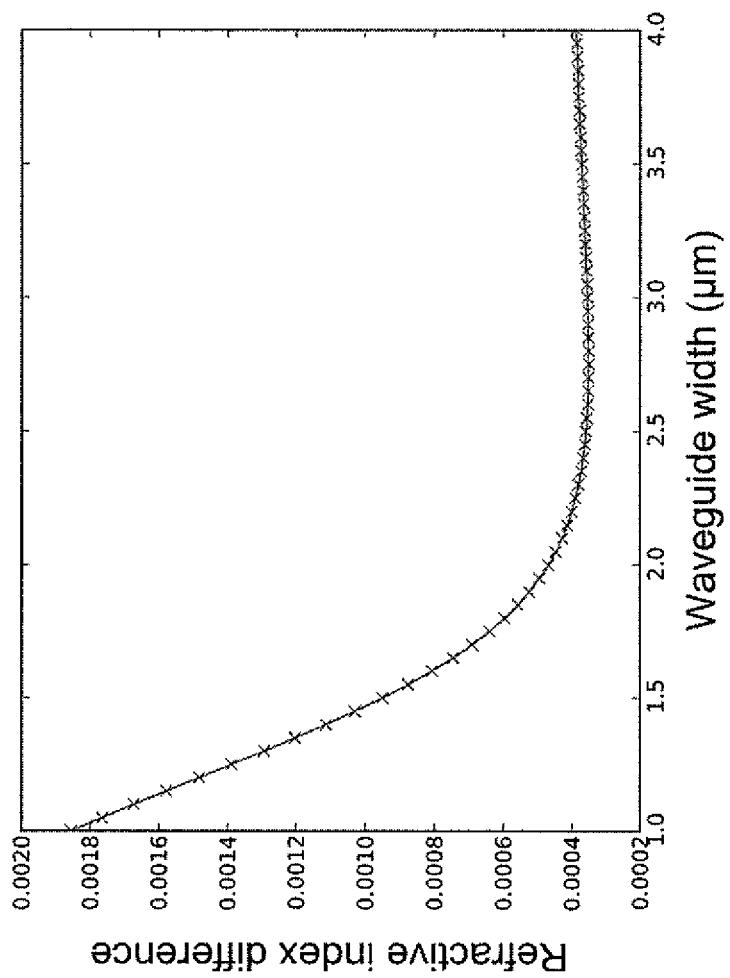

FIG. 12 illustrates a simulated difference in refractive index between polarization modes based on waveguide width.

Figure 13:
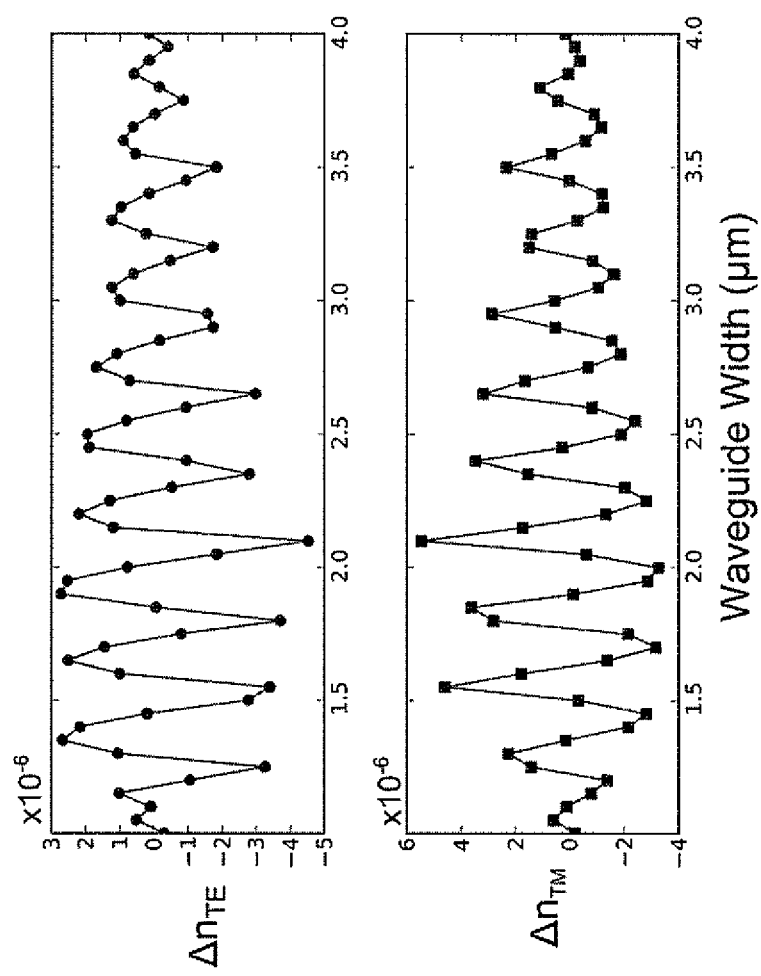

FIG. 13 illustrates a simulated error of both polarization modes vs. waveguide width.

Figure 14:
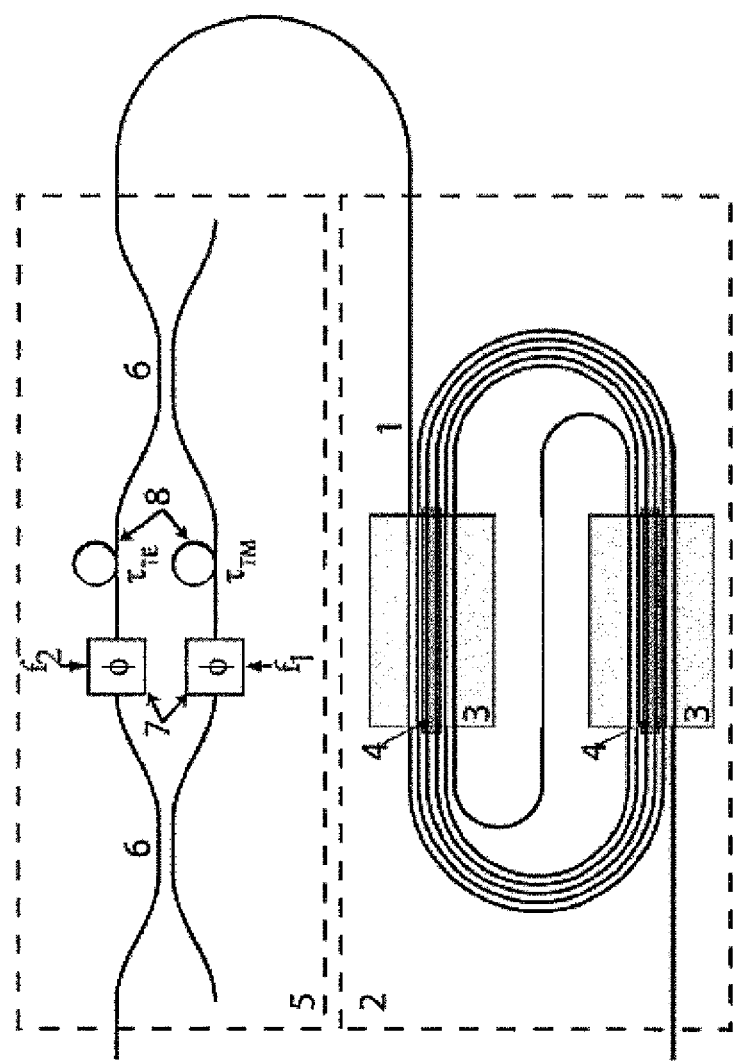

FIG. 14 illustrates an example of a variable delay system, according to an embodiment.

Figure 15A:
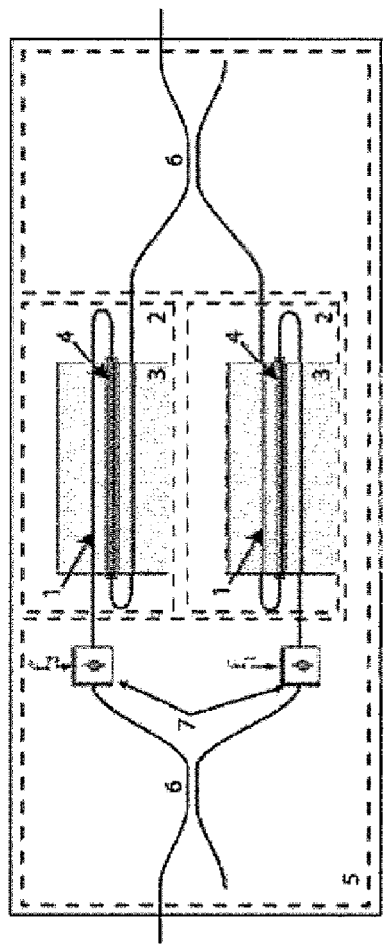
Figure 15B:
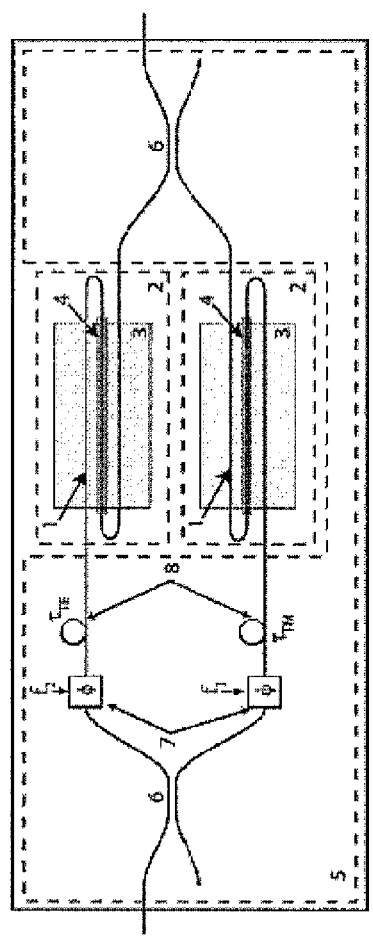

FIGS. 15A-B illustrate other examples of a variable delay system, according to embodiments.

Figure 16:
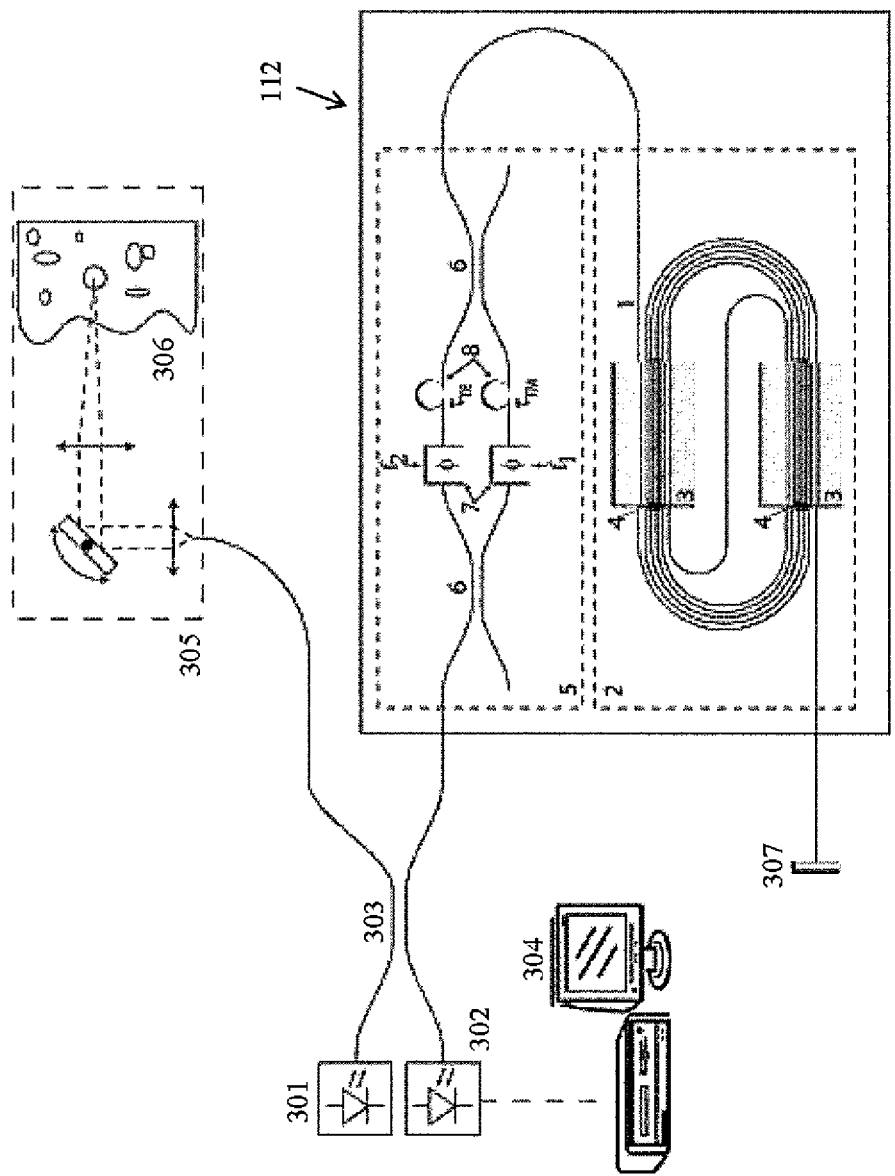

FIG. 16 illustrates an OCT system having a variable delay system, according to an embodiment.

Figure 17:
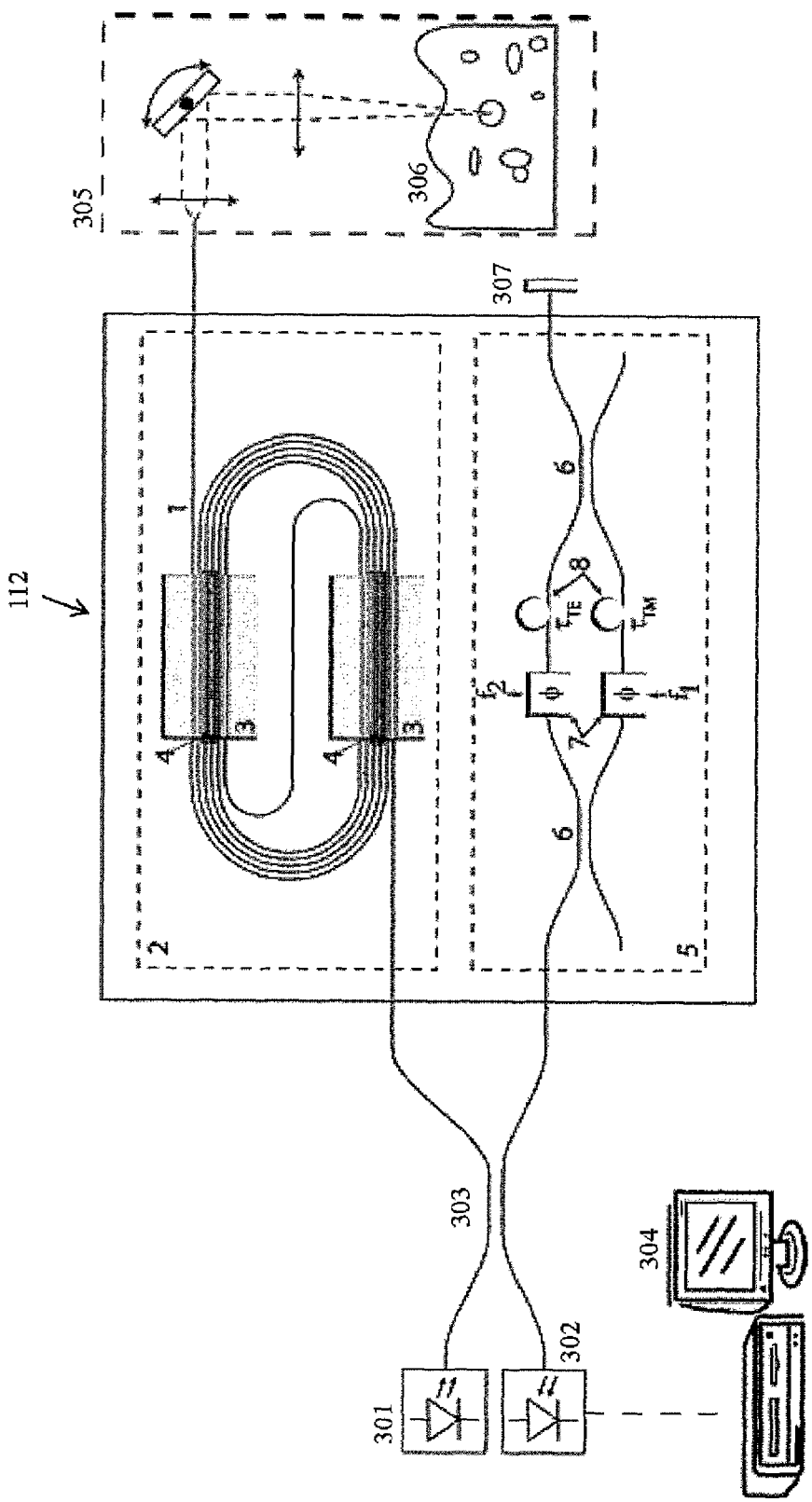

FIG. 17 illustrates an OCT system having a variable delay system, according to another embodiment.

Figure 18:
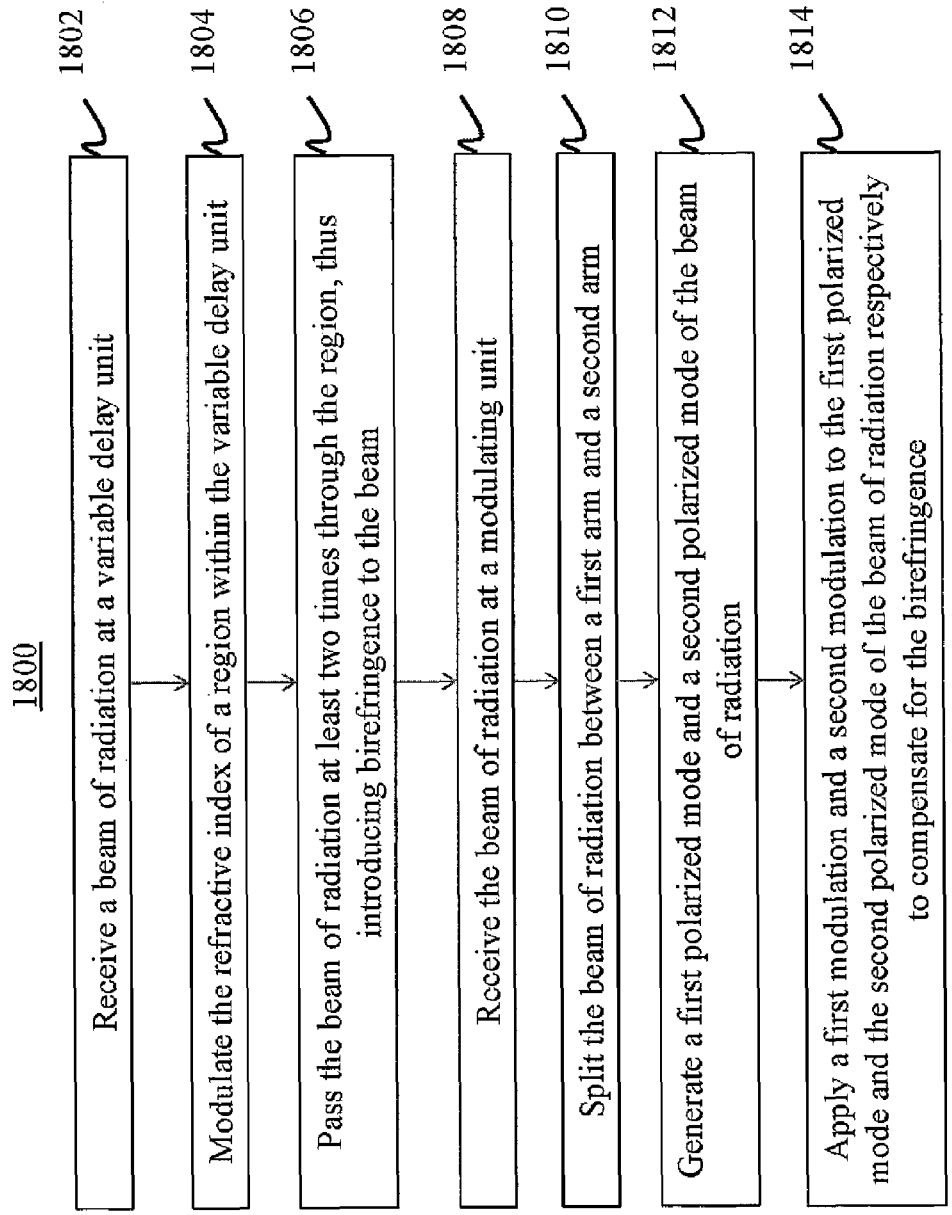

FIG. 18 depicts a method, according to an embodiment.

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Embodiments described herein provide systems and methods for introducing a group delay to a beam of radiation within an interferometric device. For example, the interferometric device may use low coherence interferometry such as optical coherence tomography (OCT) to provide image data at different depths within a sample. Varying the group delay of the light corresponds to varying a scan depth within the sample under study.

In the various embodiments described herein, the group delay is varied by controlling the index of refraction of a waveguide material that is guiding the beam of radiation. This may be achieved, for example, by having a waveguide segment perform multiple passes over at least one region where the refraction index can be controlled by active temperature changes, so that the heat produced by the heating elements is reused. Other techniques beyond generating a heat gradient may be used as well to control the refractive index, as will be described in more detail later.

By bending the waveguide along its path, multiple passes may be performed by the waveguide within the index-controlled region. However, bending of integrated waveguides leads to the appearance of birefringence, which is a source of resolution loss or even double images in OCT. As such, embodiments herein also describe systems and methods for separating or adjusting each polarization mode of the beam of radiation to overcome the effects of birefringence on the OCT image quality.

Herein, the terms "electromagnetic radiation," "light," and "beam of radiation" are all used to describe the same electromagnetic signals propagating through the various described elements and systems.

Figure 1:
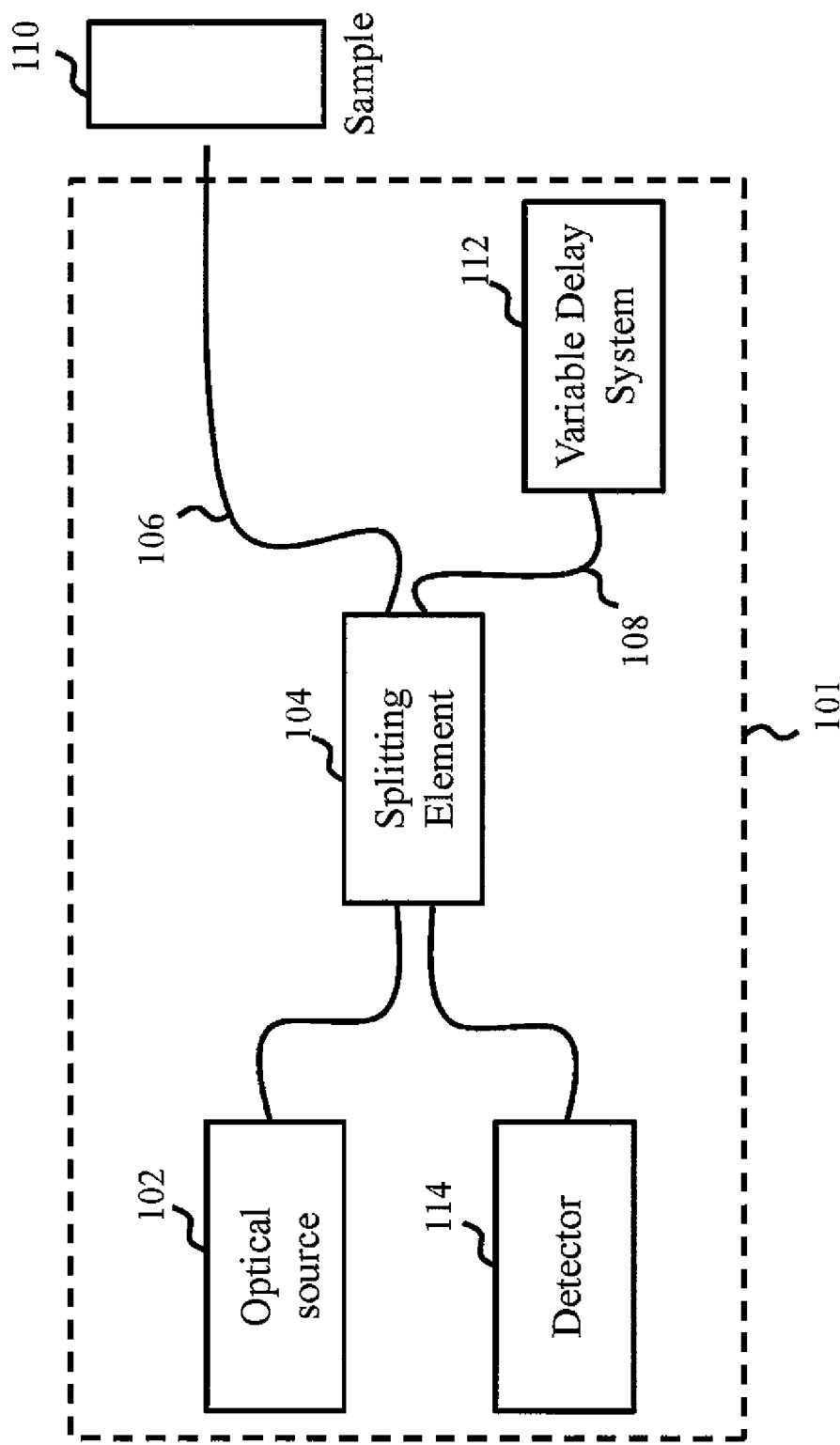
FIG. 1 illustrates a block diagram of an OCT system, according to an embodiment.

FIG. 1 illustrates an OCT system 101, utilizing a variable delay system 112, and used for imaging a sample 110, according to an embodiment. For example, variable delay system 112 may be used to provide a variable delay to the light within OCT system 101, while compensating for the effects of birefringence. The use of the term "light" may refer to any range of the electromagnetic spectrum. In an embodiment, the term "light" refers to infrared radiation at a wavelength of around 1.3 µm.

OCT system 101 further includes an optical source 102, a splitting element 104, a sample arm 106, a reference arm 108, and a detector 114. In the embodiment shown, variable delay system 112 is located within reference arm 108. However, it should be understood that variable delay system 112 may also be located in sample arm 106. Alternatively, various components of variable delay system 112 may be present in both sample arm 106 and reference arm 108. For example, components of variable delay system 112 that introduce a variable delay to the light may be located in sample arm 106 while components that modulate different polarization modes of the light to reduce birefringence may be located in reference arm 108. In one example, sample arm 106 and reference arm 108 are optical waveguides such as patterned waveguides or optical fibers. In an embodiment, all of the components of OCT system 101 are integrated onto a planar lightwave circuit (PLC). In another embodiment, at least all the components within variable delay system 112 are integrated on the same substrate of a PLC. Other implementations may be considered as well, such as, for example, fiber optic systems, free-space optical systems, photonic crystal systems, etc.

It should be understood that OCT system 101 may include any number of other optical elements not shown for the sake of clarity. For example, OCT system 101 may include mirrors, lenses, gratings, splitters, micromechanical elements, etc., along the paths of sample arm 106 or reference arm 108. Splitting element 104 is used to direct light received from optical source 102 to both sample arm 106 and reference arm 108. Splitting element 104 may be, for example, a bi-directional coupler, an optical splitter, or any other modulating optical device that converts a single beam of light into two or more beams of light.

Light that travels down sample arm 106 ultimately impinges upon sample 110. Sample 110 may be any suitable sample to be imaged, such as tissue. During an OCT procedure, the light scans at a certain depth within sample 110 and the scattered radiation is collected back into sample arm 106. In another embodiment, the scattered radiation is collected back into a different waveguide than the transmitting waveguide. The scan depth may be chosen via the delay imposed on the light within variable delay system 112.

Light within sample arm 106 and reference arm 108 is recombined before being received at detector 114. In the embodiment shown, the light is recombined by splitting element 104. In another embodiment, the light is recombined at a different optical coupling element than splitting element 104.

For the sake of clarity, variable delay system 112 is used to describe the components that introduce variable delay as well as reduce birefringence. Within variable delay system 112, one may categorize the set of components related to introducing variable delay as a variable delay unit and the set of components related to reducing birefringence as an optical modulating unit. Described herein are various embodiments for implementing both the variable delay unit and optical modulating unit.

Figure 2:
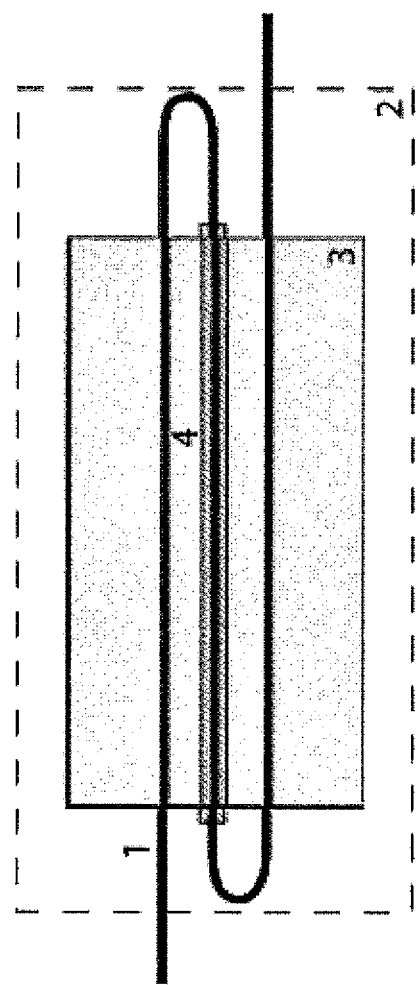
FIG. 2 illustrates a top view of a variable delay unit according to an embodiment.

FIG. 2 shows an example representation of a variable delay unit 2, according to an embodiment. In one example, a waveguide 1 makes three passes through a controllable refraction index region 3. In the illustrated embodiment, region 3 has a rectangular shape, but it should be understood that region 3 may be of any size and shape. In an embodiment, the refractive index of a material within region 3 is changed via an index modulating element, such as, for example, heating element 4. Due to the multiple passes of waveguide 1 within region 3, the heat generated by heater element 4 is reused. Such waveguide 1 placement multiplies the thermally induced variation in an optical path for a given power and size of controllable refraction index region 3.

The index-controlled material may be waveguide 1 itself, or another material within the vicinity of waveguide 1. For example, waveguide 1 may be a silicon or silicon nitride rib waveguide, where heater element 4 applies heat directly to the silicon or silicon nitride. In another example, heater element 4 applies heat to a thermally conductive material around or near waveguide 1, and the heating of the thermally conductive material generates a temperature gradient or temperature difference in waveguide 1. It should be understood that waveguide 1 is not limited to silicon-based materials as many other materials are also capable of guiding IR light, such as indium phosphide, gallium arsenide, and various tertiary or quaternary structures thereof.

FIGS. 3A-3C show example cross-sections of variable delay unit 2, according to embodiments. Each of the figures depict a design where waveguide 1 is a rib waveguide, however, other types of waveguides are possible as well, such as strip waveguides. The core waveguiding region may be surrounded by one or more cladding materials, or use the surrounding air as cladding on one or more sides.

In FIGS. 3A and 3B, waveguide 1 and heater element 4 are suspended within region 3 as a membrane, according to an embodiment. It is not required, however, that waveguide 1 be connected by the membrane across region 3. As such, waveguide 1 may traverse region 3 as a released structure. Variable delay unit 2 as depicted in FIG. 3A may be fabricated using bulk micro-machining technology to remove the substrate beneath region 3. Such techniques may include KOH etching, deep reactive ion etching (DRIE), or $XeF_2$ etching. This physical configuration of the thermally controllable refractive index region 3 increases the thermal resistance in the area below the membrane spanning across region 3, therefore minimizing the power consumed in order to modify the membrane temperature and achieve a given refractive index change. It should be understood that alternative configurations achieving the same thermal effect within the membrane could be utilized as well.

Another example of a configuration to achieve enhanced thermal performance is illustrated in FIG. 3B. In this example, waveguide 1 is suspended in region 3 over a removed portion (e.g. layer) of the substrate. This removed portion may be due to the etching of a sacrificial layer beneath the layer containing waveguide 1. The removed portion may be completely sealed beneath the layer containing waveguide 1, or it may be open to the atmosphere. In another embodiment, a material with a high thermal resistance may be disposed beneath the layer containing waveguide 1 to concentrate the heat absorption within the waveguide layer.

In another example, waveguide 1 is not suspended at all as illustrated in FIG. 3C. The desired thermal behavior in and around waveguide 1 within waveguide layer 11 can be achieved based on the choice of materials of both waveguide layer 11 and an underlying layer 12. In one embodiment, underlying layer 12 includes a material with a lower thermal conductivity and lower refractive index than a material of waveguide layer 11.

FIG. 4 illustrates an example of a variable delay unit 2 having more than one controllable refractive index region 3, according to an embodiment. In the example shown, waveguide 1 makes a plurality of passes through two separate regions 3. Each region 3 has its own heating element 4. However, it should be understood that any number of heating elements may be used to vary the index of refraction of the material within each region 3. Likewise, the present disclosure is not limited to only two controllable refractive index regions 3, but may include any number of regions 3.

FIG. 5 illustrates an example of a variable delay unit 2 having a circular controllable refractive index region 3 through which waveguide 1 makes a plurality of passes. Region 3 may have a substantially toroid shape as illustrated or may also include the middle portion and have a filled substantially circular shape.

In the previous embodiments of variable delay unit 2, heater element 4 has been implemented as an index modulating element to vary the refractive index within region 3. However, other methods beyond application of heat may be used to control the refractive index of a material. For example, heater element 4 may be replaced by an electro-optical modulating element where an applied E-field across patterned electrodes or any suitable conductive material is used to vary the index of refraction within region 3. In another example, heater element 4 may be replaced by patterned electrodes for generating charged carriers within either the waveguide material or surrounding materials. In yet another example, any combination of the above mentioned techniques for varying the index of refraction may be used within the same variable delay unit 2.

In such embodiments of variable delay unit 2, the increased yield of the controllable refractive index area 3 in terms of total optical path variation is related to the bending of waveguide 1. In an embodiment, implementing such a variable delay in a reduced space is realized by having at least some portion of waveguide 1 exhibit curvature along its path. Therefore, the bending of waveguide 1 results in the appearance of birefringence effects to the beam of radiation guided by waveguide 1.

Birefringence can cause problems in integrated optical devices. Birefringence is related to the polarization state dependency of the phase and group velocities in the waveguides. In the case of OCT systems, such a dependency can cause a relative displacement of the interference patterns of both polarization states, resulting in a loss of axial resolution, or double images received at the detector. FIG. 6 demonstrates the effect of birefringence on the mismatch between example OCT images, expressed as cΔT, collected at the detector and demodulated. The received signals displayed in the upper graph and lower graph correspond to the two polarization modes in a waveguide used in the scanning delay device. The upper graph shows the signal corresponding to the (quasi) TE mode and the lower graph contains the interference signal related to the (quasi) TM mode. Embodiments of the invention compensate for the mismatch caused by birefringence in order to improve image clarity from the data received at the detector.

In an embodiment, the variable delay system includes an optical modulating unit that provides a modulation to the phasors associated with the electromagnetic waves. In an example, the optical modulating unit actuates independently on each polarization mode of the electromagnetic wave. In one implementation, the optical modulating unit includes a combination of polarization splitting elements and modulating elements for each polarization mode.

In interferometric systems, such as OCT systems, multiplexing may be obtained through the introduction of a phase modulator that produces frequency multiplexing of the interference patterns at the detector. FIG. 7 illustrates an example of an optical modulating unit 5 with phase modulation applied to two polarization modes, according to an embodiment. Optical modulating unit 5 includes a polarization splitter 6 that splits the two polarization modes (quasi) TE and (quasi) TM through two different arms or optical paths. Subsequently, each polarization mode goes through one or more modulating elements 7 such as, for example, phase modulators. Other modulating techniques may be used as well, such as frequency modulation, amplitude modulation, etc. For a given interferometer configuration in which light crosses a delay device more than once, phase control at the modulator may be linear, with a saw-tooth signal between 0 and 7, according to an embodiment. This configuration results in a frequency shift in the interference pattern. One may design modulating elements 7 so that the interference patterns corresponding to different polarization modes are sufficiently spaced with no interference between the corresponding spectra.

In an embodiment, other modulating elements, such as group delay elements 8, are included in each arm via, for example, waveguides of different physical length, so that polarization-related mismatches in axial scan ranges can be avoided in the imaging system. The inclusion of different delays for each polarization mode may be desirable in applications where uncompensated birefringence leads to group delay differences comparable to the scan range of the imaging system being used. In this example, delay elements 8 are used to keep both polarizations within an accessible range to the variable scan device. Passive delays, such as varying waveguide length, may be replaced with active delay devices, such as those that can vary the index of refraction via applied heat, current, stress, etc.

In another embodiment, different group delay elements 8 are introduced in each arm to separate the corresponding interference signals spatially so that the axial scan in both polarizations happens sequentially along a scan cycle of the imaging system. When relating this example to OCT, the group delay difference between polarizations may be larger than the scan depth range within the sample contributing significant back-scattering signals. This delay difference may be sufficiently small so that both polarization modes can be accessed within the scan range of the OCT system.

Other multiplexing techniques may be used beyond frequency modulation. For example, code division multiplexing, time division multiplexing, etc., are all applicable to be used instead of, or along with, modulating elements 7. In the particular case of time-division multiplexing, it may be necessary to alternatively suppress, e.g. through an optical switch, one of the two polarizations. This implies some optical power loss, and potentially a penalty in signal-to-noise ratio.

FIG. 8A illustrates an example of optical modulating unit 5 where polarization splitter 6 is connected to a temporal multiplexing unit 9. For example, the temporal multiplexing unit may be implemented by using an optical switch that alternates between both polarization modes. The switching may be performed mechanically through the actual bending or movement of a waveguide, or may use an electro-optical modulator to affect the bending of the radiation beam. In another example, the thermooptic effect is used for switching between two or more optical paths.

FIG. 8B illustrates the addition of modulating elements 7 to the embodiment of FIG. 8A in order to introduce a phase modulation resulting in a frequency shift between the polarized modes, according to an embodiment. Modulating elements 7 may also affect other features of the polarized modes such as amplitude or group delay associated with the electromagnetic wave. In an embodiment, modulating elements 7 minimize interference of the inactive polarization mode due to non-ideal switching from temporal multiplexing unit 9, by further differentiating the polarization modes via, for example, frequency division multiplexing.

FIG. 9 illustrates another embodiment of optical modulating unit 5 that includes an optical absorbing element 10 for suppression of one of the polarization modes. Optical absorbing element 10 may be a material with the same refractive index as the waveguides guiding the light through either arm in optical modulating unit 5. In one example, the material of optical absorbing element 10 is a gel. Optical absorbing element 10 may include any number of structures or materials that reduce or eliminate any reflections of the impinging electromagnetic wave back through the waveguide. Although this embodiment does result in some amount of optical power loss, it also avoids potential problems when forming an image using both polarization modes. Examples of these problems include double imaging or degraded resolution due to birefringence.

In many of the aforementioned embodiments, polarization splitter 6 is designed to separate the polarization modes of an electromagnetic wave. The ability to separate both polarization modes efficiently is important for obtaining optimum system performance. In an embodiment, polarization splitter 6 may be a Mach-Zehnder interferometer with different segment widths in each arm, such as the polarization splitter illustrated in FIG. 10.

The polarization splitter illustrated in FIG. 10 includes splitting and recombination elements (201a and 201b respectively) of an interferometer, according to an embodiment. Splitting element 201a splits an incoming beam of radiation between an upper arm 202 and a lower arm 204. Although two inputs are illustrated at the entrance into splitting element 201a, the incoming beam of radiation may also be received at only one input.

Each of upper arm 202 and lower arm 204 includes waveguide segments with varying properties in order to provide a specific modulation to the light in each arm. For example, each waveguide segment may have a different geometry (e.g., varying width). In an embodiment, and to introduce sufficient design flexibility, four different waveguide segment widths ($w_1$-$w_4$) are included, with two in each arm. The corresponding waveguide lengths ($l_1$-$l_4$) are computed to obtain desired cross-coupling relations. In other words, when the light from each arm is recombined at recombination element 201b, constructive interference occurs for a given polarization and destructive interference occurs for the opposite polarization mode at one of outputs 206a and 206b. Due to the inherent 90' phase shifts in hybrid couplers, the situation will be reversed for the other output. Thus, the light exiting from the polarization splitter at outputs 206a and 206b will have a different polarization mode at each output. Equation (1) below formalizes these relations given that both arms are equal in total length.

$$\begin{bmatrix} n_{1E} & n_{3E} & -n_{2E} & -n_{4E} \\ n_{1M} & n_{3M} & -n_{2M} & -n_{4M} \\ 1 & 0 & 1 & 0 \\ 0 & 1 & 0 & 1 \end{bmatrix} \times \begin{bmatrix} l_1 \\ l_2 \\ l_3 \\ l_4 \end{bmatrix} = \begin{bmatrix} N\lambda/2 \\ M\lambda/2 \\ L_0 \\ L_0 \end{bmatrix} \quad (1)$$

In this relation, $n_{iE}$ is the effective refractive index for the TE polarization in segment i and $n_{iM}$ represents the effective refractive index for the TM polarization for segment i. These effective indices are a function of waveguide geometry. In one example, the effective indices are a function of waveguide width. FIG. 11 illustrates the simulated evolution of effective refractive index for both polarization modes as a function of waveguide width, as computed using the beam propagation method (BPM).

Waveguide segment lengths are denoted by $l_i$ and they represent two degrees of freedom in the design since each arm has the same total length. A third degree of freedom is contributed by the total interaction length $L_0$, represented by the addition of l1+l3 or l2+l4. Constructive and destructive interference conditions are represented by $N\lambda/2$ and $M\lambda/2$. In an embodiment, N and M are different by an odd integer so as to ensure polarization splitting. In one example, maximizing bandwidth is achieved by keeping M and N as small as possible.

Solving for the various parameters can be simplified using matrix calculus with the matrices defined as shown below in equation (2).

$$A = \begin{bmatrix} n_{1E} & n_{2E} & -n_{3E} & -n_{4E} \\ n_{1M} & n_{2M} & -n_{3M} & -n_{4M} \\ 1 & 0 & 1 & 0 \\ 0 & 1 & 0 & 1 \end{bmatrix}; \quad (2)$$

$$L = \begin{bmatrix} l_1 \\ l_2 \\ l_3 \\ l_4 \end{bmatrix};$$

$$X = \begin{bmatrix} N\lambda/2 \\ M\lambda/2 \\ L_0 \\ L_0 \end{bmatrix}$$

With these definitions, equation (1) can be simplified to AL=X. Given M, N and $L_0$, there are a large number of degrees of freedom left to choose a design for the polarization splitter. However, not all designs are equally valid. Indeed, at the very least, the design should be physically realistic, meaning that all lengths must be positive. This is expressed in equation (3) below.

$$l_i > 0 \, \forall i \in \{1,2,3,4\} \quad (3)$$

Once the relationships above have been established, the polarization modes may be calculated. Mode effective index calculation is especially important for imaging applications such as OCT, as accuracies up to $10^{-6}$ may be required for achieving high performance and reliability. Modes are typically calculated using BPM with a correlation approach. For these example simulations, the total interaction length has been fixed at 2 mm. This factor limits accuracy for small waveguide sections, which need long lengths for convergence, but the value has been found to offer stable solutions. Lateral grid dimensions and step size were chosen to modulate numerical errors due to discretization that results in interactions between grid elements and the rib edges of the waveguides. In one example, the BPM computed values were fitted using a 12th order polynomial to improve accuracy and to filter out numerical errors in the calculation. This also allowed the intermediate widths to be interpolated. Finally, both fits (for the TE and TM polarization modes) were subtracted from each other to obtain the refractive index difference illustrated in FIG. 12 as a function of waveguide width.

An example numerical error spectra for both polarization modes can be seen in the simulated residual plots shown in FIG. 13 for a given set of mesh settings when solving for the modes. The errors are shown to be periodic with the same periods for the TE and TM polarization modes, but with the opposite sign for a given width. It is also observed that there are many waveguide widths that exhibit refractive index error below $10^{-6}$ which could be chosen for the design and fulfill precision needs for a system such as OCT.

In addition to physical feasibility, one may optimize device manufacturability by minimizing a sensitivity of the device to errors in critical waveguide measurements, according to an embodiment. Two examples of errors to consider include changes in dimensions that affect all elements in the device equally and changes in dimensions that affect elements in the device differently. Generally, systematic errors arise due to wafer-to-wafer variation, non-uniformity over the wafer surface and statistical process variations, among other factors. Such manufacturing errors will affect all devices in a substantially similar way. Since the interaction length and area of the optical modulating unit and variable delay unit are relatively small (and waveguides are typically disposed relatively close together), differential errors may be ignored when analyzing manufacturing errors.

In an embodiment, the two fabrication dimensions that have the largest impact on the waveguide modes are the rib etching depth and the waveguide width. In one example, a change of ±50 nm is considered to be the maximum deviation that can occur during the fabrication process. If the waveguide width varies, the effective refractive index will shift. This shift may have the same sign even for waveguides of different starting sizes, but the magnitude varies according to the dependency shown in FIG. 11. This will result in a variation in matrix A from equation (2) which is represented below in equation (4). In an embodiment, for a given choice of waveguide widths (and an associated length vector), an error system matrix is obtained.

$$\Delta A = \begin{bmatrix} \Delta n_{1E} & \Delta n_{3E} & -\Delta n_{2E} & -\Delta n_{4E} \\ \Delta n_{1M} & \Delta n_{3M} & -\Delta n_{2M} & -\Delta n_{4M} \\ 0 & 0 & 0 & 0 \\ 0 & 0 & 0 & 0 \end{bmatrix} \quad (4)$$

The corresponding errors in the X vector can be derived from equation (2) in terms of the input parameters as seen below in equation (5).

$$\Delta X = \Delta A \cdot (A^{-1} \cdot X) \quad (5)$$

The total length is an input, and as such, it does not have any associated error. In an example, the errors are concentrated in the first two rows of the $\Delta X$ vector and show up as a phase shift, thus reducing the efficiency in the polarization splitting function.

An example design methodology for choosing the various waveguide widths is described herein. First, a maximum device length L is set. Next, two widths ($w_3$ and $w_4$, for example) are fixed for both arms varying between 2.6 μm and 4.0 μm. The widths of the other two variables ($w_1$ and $w_2$) are then scanned between 1.0 μm and 4.0 μm, and the system solution is found following equation (3). In parallel, a sensitivity analysis is carried out by varying all waveguide widths by 50 nm and computing matrix $\Delta A$ according to equation (4). Next, the vector $\Delta X$ is computed in agreement with equation (5). The maximum phase error for the TE and TM polarization modes is taken as the sensitivity metric and only solutions that reach a threshold phase margin over a sufficiently large number of points (e.g., 10 points) are selected as design candidates.

In an integrated imaging system, for example, an OCT system, the separation of both polarizations in frequency may be performed in either the reference arm or the sample arm. In an embodiment, the induced phase modulation (via modulating elements 7) appears additively in the respective Doppler frequencies as a differential term, thus being effective for separation purposes. For example, optical modulating unit 5 may be directly connected to variable delay unit 2 in order to produce a single device free of birefringence induced problems. However, it should be understood that other implementations are possible as well where optical modulating unit 5 is not contiguous to waveguide 1 included in variable delay unit 2.

FIG. 14 illustrates one possible integration between optical modulating unit 5 and variable delay unit 2, according to an embodiment. Together, the two units make up variable delay system 112. However, it is not required that they be directly connected by the same waveguide. In one example, optical modulating unit 5, and variable delay unit 2 are formed on the same substrate of a planar lightwave circuit (PLC). The shown variable delay unit 2 includes waveguide 1 with multiple-pass tracing over controllable refractive index regions 3. Each region 3 includes heating element 4. Optical modulating unit 5 includes polarization splitter 6, modulation elements 7, and group delay elements 8. The combination of the various elements in each arm of optical modulating unit 5 allows for the active control of birefringence through frequency separation of the polarization modes, with axial scan adjustment for the polarization states as well, according to an embodiment. Although certain embodiments of both optical modulating unit 5 and variable delay unit 2 are illustrated, it should be understood that any embodiment of either unit may be combined to achieve the same goal of variable delay system 112. Such an integrated configuration may be present in either the reference arm or sample arm of an interferometric imaging system, for example, an OCT system. Electromagnetic radiation may enter variable delay system 112 at either optical modulating unit 5 or at variable delay unit 2 and may leave via the other unit, or be reflected back and leave out the same waveguide in which it entered.

FIG. 15A illustrates another example of variable delay system 112 where birefringence is managed through separation of the polarization modes using polarization splitter 6, according to an embodiment. In this example, the polarization modes are modulated independently by modulating elements 7, and each is fed to a different variable delay unit 2. In an embodiment, each variable delay element 2 includes a separate waveguide 1 that is independently traced with multiple passes through a respective controllable refractive index region 3. One advantage to using separate variable delay units 2 is to increase the design flexibility in the case where different scan rates or scan depths for each polarization mode is desired. FIG. 15B illustrates another embodiment of variable delay system 112 similar to the one from FIG. 15A, but with added group delay elements 8 added to each polarization arm.

In one example, the extra group delay elements 8 allow for the axial scan range to be chosen independently for each polarization mode. Passive delays, such as varying waveguide length, may be replaced with active delay devices such as those that can vary the index of refraction via applied heat, current, stress, etc.

FIG. 16 illustrates an embodiment of an OCT system that incorporates one example of variable delay system 112. In an embodiment, light is generated from a source 301 and directed towards a coupler 303 via a waveguide. In one example, source 301 is a low-coherence light source. Source 301 may also be a broadband light source. Coupler 303 may be a bi-directional coupler, 50:50 coupler, or a similarly designed coupler having the capability of splitting the incoming light from source 301 into at least a sample arm and a reference arm. In an embodiment, the sample arm is connected to focusing optics 305 that sweep the received light laterally across a sample 306. In one example, the radiation scattered by sample 306 is collected again by focusing optics 305 and sent back to coupler 303. In another example, the light scattered by sample 306 is collected by a different set of optical elements than focusing optics 305. It should also be understood that the light collected from sample 306 may also be returned to a different coupler than coupler 303 in order to be recombined with the light that was split down the reference arm.

In an embodiment, light traveling down the reference arm reaches variable delay system 112 followed by a reflecting element 307. Reflecting element 307 may be a polished or cleaved facet at the end of the waveguide. Reflecting element 307 may send the light back through variable delay system 112 to coupler 303. In another example, reflecting element 307 redirects the light towards another waveguide that guides the light back to coupler 303 or to another coupler to be recombined with the light from the sample arm. In an embodiment, coupler 303 combines the return light from both arms and sends at least a portion of the recombined light to a detector 302. Detector 302 may be, for example, a photodiode or photodiode array, a CCD device, CMOS active pixel sensor, etc. Detector 302 may be operable to transform the optical interference pattern of the recombined light into an electrical output. The electrical output may then be received at a computing device 304 for further signal processing.

FIG. 17 shows another example configuration for an OCT system incorporating variable delay system 112, according to an embodiment. The depicted OCT system is similar to the system illustrated in FIG. 16, with the exception that variable delay unit 2 is located in the sample arm, while optical modulating unit 5 is located in the reference arm. As such, light directed to the sample arm first passes through variable delay unit 2 before reaching focusing optics 305, according to an embodiment. Light directed to the reference arm first passes through optical modulating element 5 before reaching reflecting element 307. FIG. 18 illustrates an example method 1800 for introducing a variable delay to a beam of radiation while reducing the effects of birefringence, according to an embodiment. Method 1800 may be performed by various components of OCT system 100, which may include a variable delay unit 2 and an optical compensating unit 5 such as those illustrated in the various aforementioned figures.

At block 1802, a beam of radiation is received at a variable delay unit. The beam of radiation may be guided to the variable delay unit within a waveguide, such as a rib waveguide on a substrate.

At block 1804, the refractive index of a region within the variable delay unit is modulated. The index may be modulated via thermo-optic or electro-optic techniques. There may be a modulating element such as a heater or an arrangement of electrodes that provide the modulation to the refractive index within the region. The refractive index of the waveguide material or a material disposed on or near the waveguide may be modulated within the region.

At block 1806, the beam of radiation is passed at least two times through the region. The passing of the beam introduces birefringence to the beam. The birefringence is caused by the inherent bending of the waveguide in order to pass the beam more than once through the region.

At block 1808, the beam of radiation is received at a modulating unit. In one example, the same waveguide that guides the beam through the variable delay unit is used to guide the beam to the modulating unit.

At block 1810, the beam of radiation is split between a first arm and a second arm. The splitting may be achieved by a splitter that is a part of an interferometer unit, such as, for example, a Mach-Zehnder interferometer.

At block 1812, a first polarized mode and a second polarized mode of the beam of radiation is generated. Each arm that the beam of radiation is split between may include modulation segments that affect the polarization state of the light when it is recombined. In one example, the modulation segments are waveguide segments of varying width. When the light is recombined, two beams are created where one beam has a first polarization mode and the other beam has a second polarization mode. The design and operation of a polarization splitter is described in more detail with reference to FIGS. 10-13.

At block 1814, a first modulation and second modulation are applied to the first polarized mode and the second polarized mode of the beam of radiation respectively. For example, a phase or frequency modulation may be applied to each polarized beam. Alternatively or in addition, a delay may be added to either or both of the polarized beams. The various modulations to the phase and/or frequency may be performed to compensate for the birefringence that was introduced to the beam of radiation. In an embodiment, the modulation to the group delay of the polarized beams is performed to separate the corresponding interference signals spatially so that an axial scan for both polarizations occurs sequentially along a scan cycle of an imaging system, such as an OCT system. Other signal modulation techniques may be performed as well to either polarized beam for performing any polarization-dependent modulation.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A system for introducing a variable group delay to a beam of radiation while compensating for the effects of birefringence on the beam of radiation, comprising:
a first waveguide and a second waveguide, wherein a first portion of a beam of radiation propagates through the first waveguide and a second portion of the beam of radiation propagates through the second waveguide, and wherein the first portion of the beam of radiation in the first waveguide is ultimately directed towards a sample;
a variable delay unit coupled to the first waveguide and configured to modulate a refractive index in a region, wherein the first waveguide makes a plurality of passes through the region; and
a polarization-dependent modulating unit coupled to the second waveguide and configured to compensate for birefringence associated with the first portion of the beam of radiation in the first waveguide, comprising:
a polarization splitter having a first arm and a second arm, the first arm including a first set of modulation segments, and the second arm including a second set of modulation segments, wherein the second portion of the beam of radiation is split between the first arm and the second arm and recombined after traversing the first set of modulation segments and the second set of modulation segments, and wherein the recombination generates a first polarized beam of radiation and a second polarized beam of radiation, and
a plurality of modulating elements configured to apply a first and second modulation to the first polarized beam of radiation and the second polarized beam of radiation respectively; and
an optical element configured to combine the first polarized beam of radiation with a beam of radiation returning from the sample and to combine the second polarized beam of radiation with the beam of radiation returning from the sample,
wherein the combination of the first polarized beam of radiation with the beam of radiation returning from the sample generates a first interference pattern and the combination of the second polarized beam of radiation with the beam of radiation returning from the sample generates a second interference pattern, and
wherein the first and second modulation applied by the plurality of modulating elements allow for multiplexing between the first interference pattern and the second interference pattern with substantially no cross-talk between the first interference pattern and the second interference pattern.

2. The system of claim 1, wherein the variable delay unit and the polarization-dependent modulating unit are formed on the same substrate of a planar lightwave circuit.

3. The system of claim 1, wherein the variable delay unit includes a heater configured to modulate an index of refraction of a material in the region via a thermo-optic effect.

4. The system of claim 1, wherein the variable delay unit includes electrodes configured to modulate an index of refraction of a material in the region via an electro-optic effect.

5. The system of claim 1, wherein the region is formed via a bulk micromachining process.

6. The system of claim 1, wherein the region is formed via a surface micromachining process.

7. The system of claim 1, wherein the variable delay unit is further configured to modulate the refractive index in a second region, wherein the first waveguide makes a plurality of passes through the second region.

8. The system of claim 1, wherein the region has a substantially circular shape.

9. The system of claim 1, wherein the first and second sets of modulation segments include waveguide segments of varying width.

10. The system of claim 1, wherein the plurality of modulating elements include group delay elements.

11. The system of claim 1, wherein the plurality of modulating elements include phase modulating elements.

12. The system of claim 1, wherein the plurality of modulating elements include amplitude modulating elements.

13. The system of claim 1, wherein the polarization-dependent modulating unit further comprises an optical switching element.

14. The system of claim 13, wherein the optical switching element is configured to switch an optical path between a waveguide associated with the first polarized beam of radiation and a waveguide associated with the second polarized beam of radiation.

15. The system of claim 1, wherein the polarization-dependent modulating unit further comprises an optical absorbing element configured to absorb either the first polarized beam of radiation or the second polarized beam of radiation.

16. An optical coherence tomography system comprising:
an optical source configured to provide a beam of radiation;
an optical element configured to split the beam of radiation between at least a first waveguide and a second waveguide, wherein a first portion of the beam of radiation propagates through the first waveguide and a second portion of the beam of radiation propagates through the second waveguide, and wherein the first portion of the beam of radiation in the first waveguide is ultimately directed towards a sample;
a variable delay unit coupled to the first waveguide, the variable delay unit configured to introduce a group delay to the first portion of the beam of radiation, and comprising an index modulating element configured to modulate a refractive index in a region, wherein the first waveguide makes a plurality of passes through the region; and
an optical modulating unit coupled to the second waveguide, the optical modulating unit comprising:
a polarization splitter configured to split the second portion of the beam of radiation into at least a first polarized beam of radiation and a second polarized beam of radiation, and
a plurality of modulating elements configured to apply a first and second modulation to the first polarized beam of radiation and the second polarized beam of radiation respectively;
wherein the optical element is further configured to combine the first polarized beam of radiation with a beam of radiation returning from the sample and to combine the second polarized beam of radiation with the beam of radiation returning from the sample, wherein the combination of the first polarized beam of radiation with the beam of radiation returning from the sample generates a first interference pattern and the combination of the second polarized beam of radiation with the beam of radiation returning from the sample generates a second interference pattern, and wherein the first and second modulation applied by the plurality of modulating elements allow for multiplexing between the first interference pattern and the second interference pattern with substantially no cross-talk between the first interference pattern and the second interference pattern.

17. The system of claim 16, further comprising a detector configured to receive the combined first polarized beam of radiation with the beam of radiation returning from the sample and the combined second polarized beam of radiation with the beam of radiation returning from the sample from the optical element.

18. The system of claim 16, wherein the index modulating element includes a heater configured to modulate an index of refraction of a material in the region via a thermo-optic effect.

19. The system of claim 16, wherein the index modulating element includes electrodes configured to modulate an index of refraction of a material in the region via an electro-optic effect.

20. The system of claim 16, wherein at least the variable delay unit and optical modulating unit are formed on the same substrate of a planar lightwave circuit.

21. The system of claim 16, wherein the region is formed via a bulk micromachining process.

22. The system of claim 16, wherein the region is formed via a surface micromachining process.

23. The system of claim 16, wherein the variable delay unit further includes a second index modulating element configured to modulate the refractive index in a second region, wherein the first waveguide makes a plurality of passes through the second region.

24. The system of claim 16, wherein the region has a substantially circular shape.

25. The system of claim 16, wherein the polarization splitter splits an incoming beam of radiation substantially between a first arm and a second arm.

26. The system of claim 25, wherein the first arm and the second arm include modulation segments.

27. The system of claim 26, wherein the modulation segments include waveguide segments of varying width.

28. The system of claim 16, wherein the plurality of modulating elements include group delay elements.

29. The system of claim 16, wherein the plurality of modulating elements include phase modulating elements.

30. The system of claim 16, wherein the plurality of modulating elements include amplitude modulating elements.

31. The system of claim 16, wherein the optical modulating unit further comprises an optical switching element.

32. The system of claim 31, wherein the optical switching element is configured to switch an optical path between a waveguide associated with the first polarized beam of radiation and a waveguide associated with the second polarized beam of radiation.

33. The system of claim 16, wherein the optical modulating unit further comprises an optical absorbing element configured to absorb either the first polarized beam of radiation or the second polarized beam of radiation.

34. The system of claim 16, wherein the optical modulating unit is configured to compensate for the effects of birefringence.

35. A method comprising:
splitting a beam of radiation between at least a first waveguide and a second waveguide, wherein a first portion of the beam of radiation propagates through the first waveguide and a second portion of the beam of radiation propagates through the second waveguide, and wherein the first portion of the beam of radiation in the first waveguide is ultimately directed towards a sample;
receiving the first portion of the beam of radiation at a variable delay unit;
modulating a refractive index of a region within the variable delay unit;
passing the first portion of the beam of radiation at least two times through the region, wherein a birefringence is introduced to the first portion of the beam of radiation via the passing;
receiving the second portion of the beam of radiation at a modulating unit;
generating a first polarized mode of the second portion of the beam of radiation and a second polarized mode of the second portion of the beam of radiation via a polarization splitter;
applying, using a plurality of modulating elements within the modulating unit, a first modulation and a second modulation to the first polarized mode and the second polarized mode of the second portion of the beam of radiation respectively; and
combining the first polarized beam of radiation with a beam of radiation returning from the sample and combining the second polarized beam of radiation with the beam of radiation returning from the sample, wherein the combination of the first polarized beam of radiation with the beam of radiation returning from the sample generates a first interference pattern and the combination of the second polarized beam of radiation with the beam of radiation returning from the sample generates a second interference pattern, and wherein the first and second modulation applied by the plurality of modulating elements allow for multiplexing between the first interference pattern and the second interference pattern with substantially no cross-talk between the first interference pattern and the second interference pattern.

* * * * *